United States Patent [19]

Dassanayake et al.

[11] Patent Number: 5,393,491
[45] Date of Patent: Feb. 28, 1995

[54] USE OF AMIDOAMINES IN OPHTHALMIC COMPOSITIONS

[75] Inventors: Nissanke L. Dassanayake, Arlington; Ronald L. Schlitzer, Forth Worth; Joonsup Park, Arlington, all of Tex.

[73] Assignee: Alcon Laboratories, Inc., Fort Worth, Tex.

[21] Appl. No.: 125,629

[22] Filed: Sep. 22, 1993

[51] Int. Cl.$^6$ ............... A01N 33/02; A61L 2/18
[52] U.S. Cl. ................ 422/28; 514/840; 424/78.04; 252/546
[58] Field of Search ............ 422/28; 252/546; 514/839, 840; 424/78.04

[56] References Cited

U.S. PATENT DOCUMENTS

| | | | |
|---|---|---|---|
| 4,407,791 | 10/1983 | Stark | 424/80 |
| 4,738,790 | 4/1988 | Miyajima et al. | 252/105 |
| 5,215,976 | 6/1993 | Fost et al. | 514/114 |

OTHER PUBLICATIONS

Muzyczko, T. M., et al., "Fatty Amidoamine Derivatives: N,N-Dimethyl-N-(3-alkylamidopropyl)amines and Their Salts," *Journal of the American Oil Chemists' Society*, vol. 45, No. 11, pp. 720–725 (1968).

*Primary Examiner*—Robert J. Warden
*Assistant Examiner*—E. Leigh Dawson
*Attorney, Agent, or Firm*—James A. Arno; Gregg C. Brown

[57] ABSTRACT

Certain amidoamines, the use of same for disinfecting and cleaning contact lenses and preserving ophthalmic products, and associated ophthalmic compositions are described.

18 Claims, No Drawings

USE OF AMIDOAMINES IN OPHTHALMIC COMPOSITIONS

BACKGROUND OF THE INVENTION

The present invention relates to the field of ophthalmology. More particularly, the invention is directed to compositions and methods for disinfecting contact lenses, and to the chemical preservation of various types of ophthalmic products. Contact lenses are exposed to a broad spectrum of microbes during normal wear and become soiled relatively quickly. Routine cleaning and disinfecting of the lenses are therefore required. Although the frequency of cleaning and disinfecting may vary somewhat among different types of lenses and lens care regimens, daily cleaning and disinfecting is normally required. Failure to clean and disinfect the lens properly can lead to a multitude of problems ranging from mere discomfort when the lenses are being worn to serious ocular infections. Ocular infections caused by particularly virulent microbes, such as *Pseudomonas aeruginosa*, can lead to loss of the infected eye(s) if left untreated or if allowed to reach an advanced stage before treatment is initiated. It is therefore extremely important that patients disinfect their contact lenses in accordance with the regimen prescribed by their optometrist or ophthalmologist.

Unfortunately, patients frequently fail to follow the prescribed regimens. Many patients find regimens to be difficult to understand and/or complicated, and as a result do not comply with one or more aspects of the regimen. Other patients may have a negative experience with the regimen, such as ocular discomfort attributable to the disinfecting agent, and as a result do not routinely disinfect their lenses or otherwise stray from the prescribed regimen. In either case, the risk of ocular infections is exacerbated.

Despite the availability of various types of contact lens disinfecting systems, such as heat, hydrogen peroxide, and other chemical agents, there continues to be a need for improved systems which: 1) are simple to use, 2) have potent antimicrobial activity, and 3) are nontoxic (i.e., do not cause ocular irritation as the result of binding to the lens material). Moreover, the chemical agents utilized in the currently marketed contact lens disinfection systems generally have limited antifungal activity. Also, many of the chemical agents currently utilized may interact with contact lens materials and/or cause irritation in some individuals. There is, therefore, a particular need in the fields of contact lens disinfection and ophthalmic composition preservation for safe and effective chemical agents having better antifungal activity. The present invention is directed to satisfaction of the above-cited needs.

SUMMARY OF THE INVENTION

The present invention is directed to methods of using certain amidoamines to disinfect contact lenses and to preserve ophthalmic compositions. The invention is also directed to contact lens disinfecting compositions which contain one or more of the subject compounds, and to various types of ophthalmic compositions (e.g., pharmaceuticals, artificial tears and comfort drops) which contain the compounds for purposes of preserving the compositions against microbial contamination.

In addition to having antimicrobial activity, including both antibacterial and antifungal activity, the compounds of the present invention are also surface active. As a result, the compounds also help to clean contact lenses by facilitating the removal of deposits from the lenses.

The amidoamines of the present invention retain their antimicrobial activity in the presence of $Na^+$, $Ca^{++}$, $Cl^-$ and other inorganic ions produced by the dissociation of alkaline and alkaline earth metal salts (e.g., sodium chloride and calcium chloride), and are compatible with polymers and surfactants frequently used in ophthalmic products, such as polyvinylpyrrolidone, and polyoxyethylene/polyoxypropylene copolymers of ethylene diamines. These properties represent significant advantages, relative to many of the antimicrobial agents previously used in the ophthalmic field.

DESCRIPTION OF PREFERRED EMBODIMENTS

The compounds used in the present invention comprise one or more compounds of the following formula, or pharmaceutically acceptable salts thereof (e.g., hydrohalide salts):

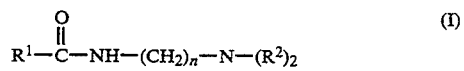

wherein:

$R^1$ is $C_6$-$C_{18}$ saturated or unsaturated alkyl, alkylaryl, or alkoxyaryl;

n is 2 to 16; and $R^2$ is $C_1$-$C_8$ saturated or unsaturated alkyl or alkanol. The compounds wherein $R^2$ is methyl or ethyl and n is 2 to 4 are particularly preferred, as are the following compounds:

| Compound No. | $R^1$ | n | $R^2$ |
| --- | --- | --- | --- |
| 1 | $C_{17}$ | 3 | $CH_3$ |
| 2 | $C_{13}$ | 2 | $CH_3$ |
| 3 | $C_{13}$ | 2 | $C_2H_5$ |
| 4 | $C_{13}$ | 3 | $CH_3$ |
| 5 | $C_{11}$ | 3 | $CH_3$ |
| 6 | $C_{11}$ | 3 | $C_2H_5$ |

The most preferred compound is Compound No. 5, which is known as N,N-Dimethyl-N'-dodecanoyl-1,3-propylenediamine.

The compounds of the present invention can be synthesized in accordance with the following reaction scheme:

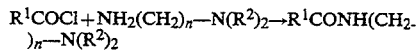

The following article may be referred to for further details concerning the synthesis of the amidoamines of formula (I): Muzyczko, et al., "Fatty Amidoamine Derivatives: N,N-Dimethyl-N-(3-alkylamidopropyl)amines and Their Salts", *Journal of the American Oil Chemists' Society*, volume 45, number 11, pages 720–725 (1968). The entire contents of the above-cited article are hereby incorporated in the present specification by reference. The above-cited article does not describe the use of compounds of formula (I) as disinfectants or preservatives in ophthalmic products, particularly products used in the care of contact lenses.

The compounds of formula (I) can be used individually, in combination with one or more other compounds of formula (I), or in combination with other disinfectants or preservatives. The compounds may, for example, be used in combination with the polymeric quaternary ammonium compounds described in U.S. Pat. No. 4,407,791; the entire contents of that patent are hereby incorporated in the present specification by reference. As described in the '791 patent, those polymeric quaternary ammonium compounds are useful in disinfecting contact lenses and preserving ophthalmic compositions.

The amount of each compound used will depend on the purpose of the use, e.g., disinfection of contact lenses or preservation of ophthalmic products, and the absence or inclusion of other antimicrobial agents. The concentrations determined to be necessary for the above-stated purposes can be functionally described as "an amount effective to disinfect" and "an amount effective to preserve" or variations thereof. The concentrations used for disinfection will generally be in the range of from about 0.0001 to about 0.1 percent by weight based on the total weight of the composition ("wt. %"). The concentrations used for preservation will generally be in the range of from about 0.00001 to about 0.01 wt. %.

The compounds of formula (I) may be included in various types of ophthalmic compositions as preservatives, so as to prevent microbial contamination of the compositions. The types of compositions which may be preserved by the compounds of formula (I) include: ophthalmic pharmaceutical compositions, such as topical compositions used in the treatment of glaucoma, infections, allergies or inflammation; compositions for treating contact lenses, such as cleaning products and products for enhancing the ocular comfort of patients wearing contact lenses; and various other types of compositions, such as ocular lubricating products, artificial tears, astringents, and so on. The compositions may be aqueous or nonaqueous, but will generally be aqueous. As will be appreciated by those skilled in the art, the compositions may contain a wide variety of ingredients, such as tonicity agents (e.g., sodium chloride or mannitol), surfactants (e.g., polyvinyl pyrrolidone and polyoxyethylene/polyoxypropylene copolymers), viscosity adjusting agents (e.g., hydroxypropyl methyl cellulose and other cellulose derivatives) and buffering agents (e.g., borates, citrates, phosphates and carbonates). The present invention is not limited with respect to the types of ophthalmic compositions in which the compounds of formula (I) may be contained as preservatives. In fact, as already noted above, the compatibility of the compounds of formula (I) with other ingredients of ophthalmic compositions, such as inorganic ions, polymers and surfactants, is a distinct advantage of the present invention, relative to antimicrobial agents previously utilized in the ophthalmic field.

As with the ophthalmic compositions of the present invention which contain one or more compounds of formula (I) as preservatives, the form of the compositions of the present invention containing one or more of the compounds for purposes of disinfecting contact lenses is not limited. The contact lens disinfecting compositions of the present invention will preferably be formulated as aqueous solutions, but may also be formulated as nonaqueous solutions, as well as suspensions, gels, and so on. The compositions may contain a variety of tonicity agents, surfactants, viscosity adjusting agents and buffering agents, as described above. The chemical compatibility of the compounds of formula (I) is also a significant advantage with respect to the use of these compounds in the contact lens disinfecting compositions of the present invention.

The above-described compositions may be used to disinfect contact lenses in accordance with processes known to those skilled in the art. More specifically, the lenses will first be removed from the eyes of the patients, and then will be immersed in the compositions for a time sufficient to disinfect the lenses. This immersion will typically be accomplished by means of soaking the lenses in a solution overnight (i.e., approximately six to eight hours). The lenses will then be rinsed and placed in the eye. Prior to immersion in the disinfecting compositions, the lenses will preferably also be cleaned and rinsed.

The compounds of formula (I) also have surface active properties. As a result of these properties, the compounds are also useful in cleaning contact lenses. More specifically, the surfactant properties of the compounds facilitate the removal of deposits typically accumulated on contact lenses when worn by human patients. These deposits vary from patient to patient, but will typically include proteins, lipids, polysaccharides and mixtures thereof, as well as various other soils which may accumulate on the lenses during normal wear and handling. The compounds will exhibit some cleaning effect even at the relatively low concentrations required for purposes of preserving ophthalmic compositions or disinfecting contact lenses. This cleaning effect is therefore useful as a supplement to the effect of other cleaning agents which may be contained in the compositions, such as anionic or nonionic surfactants. Moreover, when used at a concentration of 0.01 wt. % or higher, the compounds exhibit a more pronounced cleaning effect. The manner in which the cleaning effect of the compounds of formula (I) is utilized will depend on the type of contact lens being treated, the severity and type of the deposits on the lenses, and the overall treatment regimen used by the patient. The selection of other components for inclusion in the contact lens cleaning compositions of the present invention will also depend on these factors. The cleaning compositions will generally contain one or more of the compounds of formula (I) in an amount of at least 0.01 wt. %, and preferably from about 0.01 to 1.0 wt. %.

The above-described compositions may be used to clean contact lenses in accordance with known processes. For example, the lenses, after first being removed from the eye and preferably also rinsed, may be lightly rubbed with a small amount of the compositions between the fingers, or may be immersed in a somewhat larger volume of the compositions and then allowed to soak. The lenses are then rinsed and disinfected before being replaced in the eyes of the patients.

All of the above-described compositions will be formulated so as to be compatible with the eye and/or contact lenses to be treated with the compositions. As will be appreciated by those skilled in the art, the ophthalmic compositions intended for direct application to the eye will be formulated so as to have a pH and tonicity which are compatible with the eye. This will normally require a buffer to maintain the pH of the composition at or near physiologic pH (i.e., 7.4) and may require a tonicity agent to bring the osmolality of the composition to a level at or near 300–320 milliosmoles. The formulation of compositions for disinfecting and/or cleaning contact lenses will involve similar considerations, as well as considerations relating to the physical effect of the compositions on contact lens materials and the potential for binding or absorption of the components of the composition by the lens.

The compositions and methods of the present invention, may be used in conjunction with various types of contact lenses, including both lenses generally classified as "hard" and lenses generally classified as "soft".

The following examples are presented to further illustrate methods of synthesizing the amidoamies utilized in the present invention:

EXAMPLE 1

N,N-Dimethyl-N'-Dodecanoyl-1,3-Propylenediamine (Compound No. 5)

A 500 ml RB flask containing a solution of lauroyl chloride (19.38 g., 89 mM) in dry chloroform (200 ml) was cooled to 0° C. on an ice bath. A solution of N,N-dimethyl-1,3-propanediamine (10.40 g., 51 mM) and triethylamine (9.40 g., 93 mM) in dry chloroform (25ml) was added dropwise to the cold solution through an addition funnel, then allowed to warm to room temperature and stirred for 2 hours. The chloroform was removed under reduced pressure and the residue redissolved in an ethanol/water mixture (1:1) and neutralized with sodium bicarbonate, followed by extraction with chloroform (4×50 ml). The combined extracts were dried (MgSO$_4$), concentrated, and the residue distilled under reduced pressure (bp 171° C., 10μ) to give 23.92 g. (68%) of the subject compound as an amber solid.

PMR (200 MHz, CDCl$_3$): δ3.33 (q, 2 H, NH—CH$_2$), 3.37 (t, 2H, CH$_2$N(CH$_3$)$_2$), 2.23 (s, 6 H,N(CH$_3$)$_2$), 2.15 (t, 2 H, CH$_2$CO), 1.62 (m, 4 H, CH$_2$CH$_2$CO, CH$_2$CH$_2$N(CH$_3$)$_2$), 1.26 (s, 16 H, —CH$_2$—), 0.88 (t, 3 H). Analysis: Calculated for C$_{17}$H$_{36}$N$_2$O: C, 71.77; H, 12.75; N, 9.85. Found: C, 72.06; H, 12.76; N, 9.94. IR (neat): 3280, 2910, 2840, 2800, 2750, 1460, 1370, 1260, 1125, 1035 cm$^{-1}$.

EXAMPLE 2

N,N-Dimethyl-N'-Tetradecanoyl-1,3-Propylenediamine (Compound No. 4)

2.0 g. (0.0196 moles) of 3-dimethylaminopropylamine in 40 ml chloroform was added dropwise to an ice cold chloroform solution (50 ml) of myristoyl chloride (4.17 g., 0.0169 moles). After addition, the ice bath was removed and the solution was stirred for 2 hours. A 25 ml aqueous sodium bicarbonate solution was added and stirred for 30 minutes. The organic layer was then washed with 30 ml aqueous sodium bicarbonate/sodium chloride solution and dried with magnesium sulfate. The solution was concentrated in vacuo and the amide was recrystallized in ethyl acetate to yield 3.29 g. (0.0105 moles, 62.3%) of the subject compound.

PMR (200 MHz, CDCL$_3$): δ6.9 (s, 1H, NH), 3.3 (q, 3H, NHCH$_2$), 2.4 (t, 2H, NCH$_2$), 2.22 (s, 6H, NCH$_3$), 2.15 (t, 2H, COCH$_2$), 1.7-1.5 (m, 4H, COCH$_2$CH$_2$ and NHCH$_2$CH$_2$), 1.25 (s, 20H, COCH$_2$CH$_2$(CH$_2$)$_{10}$), 0.88 (t, 3H, CH$_3$). Elemental Analysis: Calculated for C$_{19}$H$_{40}$N$_2$O (312.52): C, 73.02; H, 12.90; N, 8.96. Found: C, 72.96; H, 12.92; N, 8.93

EXAMPLE 3

N,N-Diethyl-N'-Tetradecanoyl-1,2-Ethylenediamine (Compound No. 3)

8.35 g. (0.072 moles) of diethylethylenediamine in 40 ml chloroform was added dropwise to an ice cold chloroform solution (60 ml) of myristoyl chloride (15.84 g., 0.064 moles). After addition, the ice bath was removed and the solution stirred for 6 hours. The reaction mixture was then stirred with aqueous sodium bicarbonate for 10 minutes and the organic layer was washed with an aqueous sodium bicarbonate/sodium chloride solution. The organic layer was then dried over magnesium sulfate and concentrated in vacuo leaving a white solid. The amide was recrystallized in ethyl acetate, filtered and dried to yield 16.58 g. (0.051 moles, 79.1%) of the subject compound.

PMR (200 MHz, CDCl$_3$): δ6.2 (s, 1H, NH), 3.3 (q, 2H, NHCH$_2$), 2.6-2.5 (m, 6H, NCH$_2$), 2.2 (t, 2H, COCH$_2$), 1.6 (m, 2H, COCH$_2$CH$_2$), 1.25 (s, 20H, COCH$_2$CH$_2$(CH$_2$)$_{10}$), 1.03 (t, 6H, NCH$_2$CH$_2$CH$_3$), 0.88 (t, 3H, CH$_3$). Elemental Analysis: Calculated for C$_{20}$H$_{42}$N$_2$O (326.54): C, 73.56; H, 12.96; N, 8.58 Found: C, 73.44; H, 12.97; N, 8.56

EXAMPLE 4

N,N-Diethly-N'-Dodecanoyl-1,3-Propylenediamine (Compound No. 6)

A 500 ml RB flask containing a solution of lauroyl chloride (19.03 g., 87 mM) in dry chloroform (200 ml) was cooled to 0° C. on an ice bath. A solution of N,N-diethly-1,3-propanediamine (15.00 g., 115 mM) in dry chloroform (25 ml) was added dropwise to the cold solution then allowed to warm to room temperature and stirred for 2 hours. The chloroform was removed under reduced pressure and the residue redissolved in an ethanol/water mixture (1:1) and neutralized with sodium bicarbonate, followed by extraction with chloroform (4×50 ml). The combined extracts were dried (MgSO$_4$), concentrated, and the residue distilled under reduced pressure (bp 176° C., 20μ) to give 21.47 g. (79%) of the subject compound as an amber oil.

PMR (200 MHz. CDCl$_3$): δ3.33 (q, 2 H,NH—CH$_2$), 2.52 (m, 6 H, CH$_2$N(CH$_2$CH$_3$)$_2$), 2.15 (t, CH$_2$CO), 1.63 (m, 4 H, CH$_2$CH$_2$CO, CH$_2$CH$_2$N(CH$_2$CH$_3$)$_2$), 1.25 (s, 16 H, —CH$_2$—), 1.04 (t, 6 H, N(CH$_2$CH$_3$), 0.88 (t, 3 H, —CH$_3$). IR (neat): 3280, 3080, 2910, 2840, 2800, 2750, 1640, 1550, 1460, 1370, 1280, 1100, 1060 cm$^{-1}$. MS (Cl): m/e 313 (MH+)

The following examples are presented to further illustrate ophthalmic compositions which may contain one or more of the compounds of formula (I):

EXAMPLE 5

The following formulation might serve as a vehicle for an ophthalmic drug. The formulation would contain one or more compounds of formula (I) as a preservative.

| Ingredient | Amount (wt. %) |
| --- | --- |
| Sodium Chloride | 0.5% |
| Mannitol | 2.5% |
| HEPES | 0.119% |
| NaOH/HCl | pH 7.0 |
| Purified water | QS 100 |

EXAMPLE 6

The following formulation may be utilized as a contact lens disinfecting solution. The formulation would contain one or more compounds of formula (I) as a disinfectant.

| Ingredient | Amount (wt. %) |
|---|---|
| Mannitol | 0.64% (w/v) |
| Boric Acid | 0.225% |
| Sodium Borate | 0.08% |
| Sodium Citrate | 0.46% |
| Citric Acid | 0.016% |
| Sodium Chloride | 0.48% |
| Disodium Edetate | 0.05% |
| NaOH/HCl | pH 7.0 |
| Purified Water | QS 100 |

EXAMPLE 7

The following formulation, which would contain one or more compounds of formula (I), may be utilized as a contact lens disinfecting solution, and would also aid in the cleaning of the lens.

| Ingredient | Amount (wt. %) |
|---|---|
| Boric Acid | 0.58% |
| Sodium Borate | 0.18% |
| Sodium Chloride | 0.49% |
| Disodium Edetate | 0.05% |
| Poloxamine | 0.1% |
| NaOH/HCl | pH 7.0 |
| Purified Water | QS 100% |

What is claimed is:

1. A preserved pharmaceutical composition comprising an ophthalmic composition and an amount of a compound of the following formula effective to preserve said ophthalmic composition from microbial contamination:

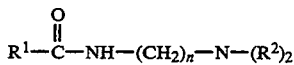

wherein:
$R^1$ is $C_6$-$C_{18}$ saturated or unsaturated alkyl, alkylaryl, or alkoxyaryl;
n is 2 to 16; and
$R^2$ is $C_1$-$C_8$ saturated or unsaturated alkyl or alkanol, or a pharmaceutically acceptable salt thereof.

2. A composition according to claim 1, wherein n is 2 to 4.

3. A composition according to claim 1, wherein $R^1$ is heptadec-8-enyl, undecyl, undecenyl, pentadecyl or heptadecyl; and $R^2$ is methyl, ethyl or hydroxyethyl.

4. A composition according to claim 1, wherein $R^1$ is heptadec-8-enyl, n is 2, and $R^2$ is ethyl.

5. An ophthalmic composition comprising an amount of a compound of the following formula effective to disinfect contact lenses:

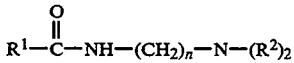

wherein:
$R^1$ is $C_6$-$C_{18}$ saturated or unsaturated alkyl, alkylaryl, or alkoxyaryl;
n is 2 to 16; and
$R^2$ is $C_1$-$C_8$ saturated or unsaturated alkyl or alkanol, or a pharmaceutically acceptable salt thereof; and a pharmaceutically acceptable vehicle therefor.

6. A composition according to claim 5, wherein n is 2 to 4.

7. A composition according to claim 5, wherein $R^1$ is heptadec-8-enyl, undecyl, undecenyl, pentadecyl or heptadecyl; and $R^2$ is methyl, ethyl or hydroxyethyl.

8. A composition according to claim 5, wherein $R^1$ is heptadec-8-enyl, n is 2, and $R^2$ is ethyl.

9. A method of disinfecting a contact lens which comprises immersing the lens in an antimicrobial composition for a time sufficient to disinfect the lens, said composition comprising an amount of a compound of the following formula effective to disinfect the lens:

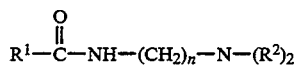

wherein:
$R^1$ is $C_6$-$C_{18}$ saturated or unsaturated alkyl, alkylaryl, or alkoxyaryl;
n is 2 to 16; and
$R^2$ is $C_1$-$C_8$ saturated or unsaturated alkyl or alkanol, or a pharmaceutically acceptable salt thereof; and a pharmaceutically acceptable vehicle therefor.

10. A method according to claim 9, wherein n is 2 to 4.

11. A method according to claim 9, wherein $R^1$ is heptadec-8-enyl, undecyl, undecenyl, pentadecyl or heptadecyl; and $R^2$ is methyl, ethyl or hydroxyethyl.

12. A method according to claim 9, wherein $R^1$ is heptadec-8-enyl, n is 2, and $R^2$ is ethyl.

13. A method of preserving an ophthalmic composition which comprises including in the composition an amount of a compound of the following formula effective to preserve the composition from microbial contamination:

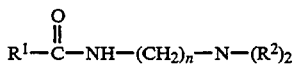

wherein:
$R^1$ is $C_6$-$C_{18}$ saturated or unsaturated alkyl, alkylaryl, or alkoxyaryl;
n is 2 to 16; and
$R^2$ is $C_1$-$C_8$ saturated or unsaturated alkyl or alkanol, or a pharmaceutically acceptable salt thereof.

14. A method according to claim 13, wherein n is 2 to 4.

15. A method according to claim 13, wherein $R^1$ is heptadec-8-enyl, undecyl, undecenyl, pentadecyl or heptadecyl; and $R^2$ is methyl, ethyl or hydroxyethyl.

16. A method according to claim 13, wherein $R^1$ is heptadec-8-enyl, n is 2, and $R^2$ is ethyl.

17. A method of cleaning a contact lens which comprises contacting the surfaces of the lens with a composition comprising an amount of a compound of the following formula effective to clean the lens:

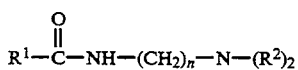
wherein:
$R^1$ is $C_6$-$C_{18}$ saturated or unsaturated alkyl, alkylaryl, or alkoxyaryl;
n is 2 to 16; and
$R^2$ is $C_1$-$C_8$ saturated or unsaturated alkyl or alkanol, or a pharmaceutically acceptable salt thereof; and a pharmaceutically acceptable vehicle thereof.
18. A method according to claim 17, wherein the concentration of said compound is at least 0.01 wt. %.
* * * * *